(12) United States Patent
Bobal et al.

(10) Patent No.: US 7,932,403 B2
(45) Date of Patent: Apr. 26, 2011

(54) PROCESS FOR PREPARING PYRROLE DERIVATIVES AND INTERMEDIATES

(75) Inventors: Pavel Bobal, Malacky (SK); Jaroslav Frantisek, Brno (CZ); Jiri Stohandl, Bobrova (CZ); Kane Denike, Georgetown (CA); Armin Boerner, Rostock (DE); Vitali Tararov, Moscow (RU); Andrei Korostylev, Ryazan (RU); Gerd Koenig, Zwickau (DE); Nicolas Jeker, Dornach (CH)

(73) Assignee: ratiopharm GmbH, Ulm (DE)

( * ) Notice: Subject to any disclaimer, the term of this patent is extended or adjusted under 35 U.S.C. 154(b) by 324 days.

(21) Appl. No.: 11/722,318

(22) PCT Filed: Dec. 16, 2005

(86) PCT No.: PCT/EP2005/013588
§ 371 (c)(1),
(2), (4) Date: Oct. 29, 2007

(87) PCT Pub. No.: WO2006/066823
PCT Pub. Date: Jun. 29, 2006

(65) Prior Publication Data
US 2009/0012312 A1    Jan. 8, 2009

(30) Foreign Application Priority Data
Dec. 20, 2004  (EP) .................... 04030159

(51) Int. Cl.
C07D 207/33    (2006.01)
C07D 207/335   (2006.01)
(52) U.S. Cl. ......... 548/530; 548/531; 548/562; 548/563
(58) Field of Classification Search .................... 548/400
See application file for complete search history.

(56) References Cited

U.S. PATENT DOCUMENTS
5,969,156 A * 10/1999 Briggs et al. .................. 548/537
6,867,306 B2 *  3/2005 Srinath et al. ................. 548/517
2004/0259880 A1* 12/2004 Lockhart et al. ......... 514/252.16

FOREIGN PATENT DOCUMENTS
| WO | WO03/004457  | 1/2003 |
| WO | WO03/044011  | 5/2003 |
| WO | WO2004/106299 | 12/2004 |
| WO | WO2005/012246 | 2/2005 |
| WO | WO2005/118536 | 12/2005 |

OTHER PUBLICATIONS

Patini et al, Chem Rev, 1996, 3147-3176, esp. p. 3150.*
Graul, A et al., Drugs of the Future, vol. 22(9): 956-968 (1997).
Pandey, PS et al., Bioorganic & Medicinal Chemistry Letters, vol. 14(1): 129-131 (Jan. 2004).
Procopiou, PA et al., Journal of Medicinal Chemistry (ACS), vol. 36(23): 3658-3662 (1993).
Roth, BD et al., Journal of Medicinal Chemistry (ACS), vol. 34(1): 357-366 (Jan. 1991).
International Search Report for PCT/EP05/013588 (PCT/ISA/210).
Written Opinion of the International Searching Authority for PCT/EP05/013588 (PCT/ISA/237).

* cited by examiner

*Primary Examiner* — Yong Chu
*Assistant Examiner* — Michael Barker
(74) *Attorney, Agent, or Firm* — Chalin Smith; Smith Patent Consulting, LLC

(57) ABSTRACT

The present invention relates to a process for preparing pyrrole derivatives of a class that is effective at inhibiting the biosynthesis of cholesterol in humans, and more particularly to improved synthetic methods for preparing 3,5-dihydroxy-7-pyrrol-1-yl heptanoic acids from 1,4-diketo starting materials. The invention further relates to intermediates in this process formula (I).

(I)

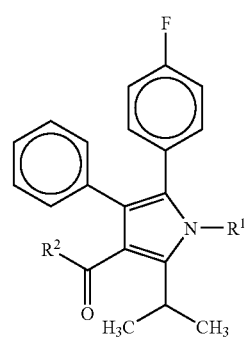

10 Claims, No Drawings

PROCESS FOR PREPARING PYRROLE DERIVATIVES AND INTERMEDIATES

This application corresponds to the national phase of PCT Application No. PCT/EP05/013588, filed Dec. 16, 2005, which, in turn, claims priority to European Patent Application No. 04.030159.0, filed Dec. 20, 2004, the contents of which are incorporated by reference herein in its entirety.

The present invention relates to a process for preparing pyrrole derivatives of a class that is effective at inhibiting the biosynthesis of cholesterol in humans, and more particularly to improved synthetic methods for preparing 3,5-dihydroxy-7-pyrrol-1-yl heptanoic acids from 1,4-diketo starting materials. The invention further relates to intermediates in this process.

It is known that certain 3,5-dihydroxy heptanoic acid derivatives are competitive inhibitors of the 3-hydroxy-3-methyl-glutaryl-coenzyme A ("HMG-CoA"). HMG-CoA is a key enzyme in the biosynthesis of cholesterol in humans. Its inhibition leads to a reduction in the rate of biosynthesis of cholesterol. The first HMG-CoA inhibitor to be described is compactin ([1S-[1α(R*),7β,8β(2S*,4S*),8αβ]]-1,2,3,7,8a-hexahydro-7-methyl-8-[2-(tetrahydro-4-hydroxy-6-oxo-2H-pyran-2-yl)ethyl]-1-naphthalenyl 2-methylbutanoate), which was isolated from cultures of *Penicillium* in 1976. In 1987, lovastatin ([1S-[1α(R*),3α,7β,8β(2S*,4S*),8αβ]]-1,2,3,7,8,8a-hexahydro-3,7-dimethyl-8-[2-(tetrahydro-4-hydroxy-6-oxo-2H-pyran-2-yl)ethyl]-1-naphthalenyl 2-methylbutanoate) became the first HMG-CoA reductase inhibitor approved by the Food and Drug Administration (FDA) for treatment of hypercholesterolemia. Both compactin and lovastatin are derived from bacterial cultures.

Two other naturally-derived HMG-CoA reductase inhibitors, simvastatin and pravastatin are structurally related to compactin and lovastatin.

In 1987, it was reported in U.S. Pat. No. 4,681,893 that compounds within a certain class of 3,5-dihydroxy-7-pyrrol-1-yl heptanoic acid (and the corresponding lactones) also were effective at inhibiting the HMG-CoA reductase enzyme. One such compound is [R(R*,R*)]-2-(4-fluorophenyl)-β,δ-dihydroxy-5-(1-methylethyl)-3-phenyl-4-[(phenylamino)carbonyl]-1H-pyrrole-1-heptanoic acid ("atorvastatin"), which was said to provide surprising inhibition in U.S. Pat. No. 5,273,995. Atorvastatin later received FDA approval as an adjunct to a low cholesterol diet to reduce elevated levels of total cholesterol, low density lipoprotein cholesterol, apo B and triglycerides and to increase levels of high density lipoprotein cholesterol in patients with hyperlipidemia.

In contrast to compactin, lovastatin, simvastatin and pravastatin, there is no known fermentation culture that produces atorvastatin. It, and other 3,5-dihydroxy-7-pyrrol-1-yl heptanoic acids, must be synthesized by traditional synthetic methods.

A number of processes for the synthesis of 3,5-trihydroxy-7-pyrrol-1-yl heptanoic acids and in particular atorvastatin are known. Some of the processes are concerned with the synthesis of the 3,5-dihydroxy heptanoic acid side chain of the pyrrole ring while others are concerned with the formation of the pyrrole ring.

For example, EP-A-0 330 172 teaches that the pyrrole ring can be formed by the Paal-Knorr reaction between an 1,4-diketone and a primary amine being a precursor of the 3,5-dihydroxy heptanoic acid side chain. The 1,4-diketone already bears those substituents required at the pyrrole ring of atorvastatin and in particular the (phenylamino)carbonyl group required at position 4 of the pyrrole ring.

WO 2004/046105 also discloses a process comprising the Paal-Knorr reaction between a ketal-protected 7-amino-3,5-dihydroxy-1-heptanol and an 1,4-diketone. Also this diketone already comprises the aminocarbonyl functionality required at position 4 of the pyrrole ring in atorvastatin.

Similar reactions are disclosed in EP-A-0 687 263, WO 02/057274 and WO 03/004457. All these synthesis routes have in common that the Paal-Knorr reaction is conducted with an 1,4-diketone comprising an amino carbonyl moiety and in particular (phenylamino)carbonyl at the position required to finally obtain atorvastatin.

It is, however, difficult to obtain the required 1,4-diketone comprising the amino carbonyl moiety in good yield and purity. Moreover, even when starting from a commercially available 1,4-diketone precursor comprising the required (phenylamino)carbonyl side chain, it turned out to be difficult, if not impossible, to replace the phenylamino residue by other residues such as alkoxy or aryloxy residues without cleavage of the diketone. This limits the possible variation of the substituents and makes a screening for new compounds for inhibiting the biosynthesis of cholesterol in humans difficult.

Therefore, there is still a need for further methods of synthesizing pyrrole derivatives and in particular 3,5-dihydroxy-7-pyrrol-1-yl heptanoic acids having HMG-CoA inhibitory activity.

1,3-dipolar cycloaddition reactions of mesoionic munchnone (1,3-oxazolium-5-olate) with ethyl phenylpropiolate and N1,3-diphenyl-2-propynamide are described by P. S. Pandey et al., in Bioorganic & Medicinal Chemistry Letters 14 (2004) 129-131. The reaction of mesoionic munchnone with ethyl phenylpropiolate is found to be regioselective giving 1:9 ratio of regioisomers 8a and 8b

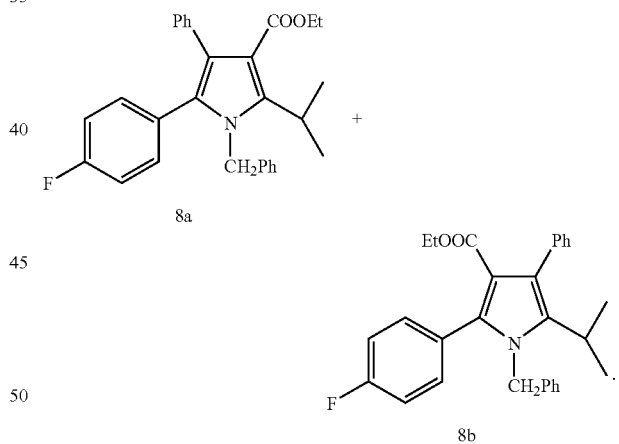

This reaction is, however, said to be undesirable, because 8a is the desired isomer for preparing atorvastatin. The document therefore suggests to carry out the reaction of the mesoionic munchnone with N1,3-diphenyl-2-propionamide, because this reaction is not regioselective and, thus, gives a higher yield of the desired isomer.

Thus, an object of the present invention is to provide a further process for preparing pyrrole derivatives and in particular 3,5-dihydroxy-7-pyrrol-1-yl heptanoic acids. The intermediates in the process should be obtainable in good yield and purity. Moreover, the process should be suitable for an industrial scale. Furthermore, the process and the intermediates should provide the option to easily modify the side chain on the carbonyl substituent at position 4 of the pyrrole ring of atorvastatin to make the screening of compounds bearing different substituents easier.

It has now surprisingly been found that the above problems can be overcome by a process for preparing a pyrrole derivative of the formula I

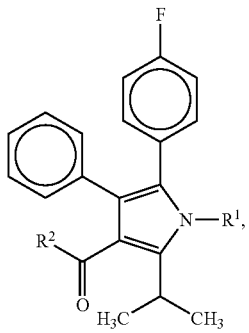

I wherein
$R^1$ is hydrogen or a straight or branched, saturated or unsaturated $C_{1-30}$ hydrocarbon group which may comprise 1-5 oxygen atoms, 1-5 nitrogen atoms, 1-2 sulfur atoms, 1 selenium atom and/or 1-5 —$NR^6$— residues, which hydrocarbon group may be substituted with 1-5 optionally protected hydroxy groups, 1-5 —$OR^7$ residues, 1-5 —$NR^8R^9$ residues, 1-5 halogen atoms and/or 1-5 optionally protected carboxy groups, in which hydrocarbon group 1-5 carbon atoms may form carbonyl groups and which hydrocarbon group or part of which hydrocarbon group may form one or more rings (such as lactones, lactames or oxazolidines),
$R^2$ is —$OR^3$, —$NR^4R^5$, —$NR^{10}NR^{11}R^{12}$, —$NR^{13}OR^{14}$, —$ONR^{15}R^{16}$ or halogen,
$R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are independently selected from hydrogen or a straight, branched and/or cyclic, saturated or unsaturated $C_{1-10}$ alkyl residue or aryl residue, both residues being optionally substituted with 1-3 optionally protected hydroxy or carboxy groups, 1-3 —$OR^7$ residues, 1-3 —$NR^8R^9$ residues and/or 1-3 halogen atoms, the $C_{1-10}$ alkyl residue optionally comprising 1-3 oxygen atoms, 1-3 nitrogen atoms and/or 1-3 —$NR^6$— residues, the $C_{1-10}$ alkyl residue further optionally comprising or being substituted with 1 or 2 aryl residues,
or a salt thereof,
which process comprises the steps of reacting a compound of the formula II

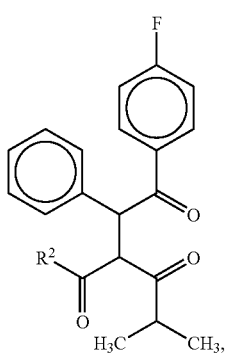

II wherein $R^2$ is defined as above, or a salt thereof with a compound of the formulae IIIa, IIIb or IIIc $R^1$—$NH_2$  IIIa, $R^1$—NH—COO$^-$H$_3$N$^+$—$R^1$  IIIb, $R^1$—NH—Si$R^{17}R^{18}R^{19}$  IIIc, or mixtures thereof, wherein $R^1$ is defined as above,
$R^{17}$ and $R^{18}$ are independently selected from straight, branched and/or cyclic $C_{1-10}$ alkyl residues or aryl residues, and
$R^{19}$ is straight, branched and/or cyclic $C_{1-10}$ alkyl residue, aryl residue or —NH—$R^1$,
and, if necessary, converting the obtained pyrrole derivative having the substituent $R^1$ into a pyrrole derivative having a different substituent $R^1$,
provided that if $R^2$ is —$NR^4R^5$ the compound of the formula IIIa is $NH_3$.

Preferably the compound of the formula IIIa is not

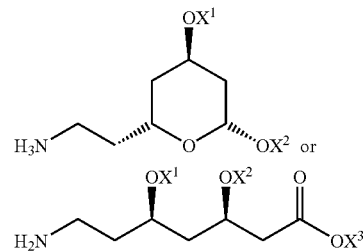

wherein $X^1$, $X^2$ and $X^3$ are hydrogen or protecting groups, in particular if $R^2$ is —$OR^3$ (such as —$OCH_2CH_3$).

One advantage of the process of the present invention is that if $R^2$ is —$OR^3$ or halogen the compound of the formula II is easy to produce in good yield and purity. A further advantage is that if $R^2$ is —$OR^3$ or halogen the intermediate compound of the formula II provides the possibility of easy substitution of the $R^2$ residue, thereby providing higher flexibility for example for screening substituted pyrrole compounds for their pharmaceutical activity. This finding is particularly unexpected, since the corresponding known diketone anilide (2-[2-(4-fluorophenyl)-2-oxo-1-phenyl-ethyl]-4-methyl-3-oxo-pentanoic acid phenylamide) turned out to be stable to hydrolysis. It reacts with base and hydrogen peroxide not to the expected acid but it breaks to 1-(4-fluorophenyl)-2-phenylethan-1-one (compound of formula VIII). This problem does not arise when using the corresponding diketone ester or acid halogenide (compound of the formula II).

Moreover, if using $NH_3$ as the compound of the formula IIIa in the process of the present invention, the yield of the ring-forming reaction is significantly higher compared to reactions with compounds of the formula IIIa, wherein $R^1$ is other than hydrogen.

In the process of the present invention a compound of the above formula II is reacted with a compound of the above formulae IIIa, IIIb or IIIc. In the compound of the formulae IIIa, IIIb and IIIc $R^1$ is either hydrogen or a hydrocarbon group. If in the compound of formula IIIa $R^1$ is hydrogen, liquid ammonia, aqueous ammonia or a solution of an ammonium salt such as $NH_4Cl$ or $CH_3COONH_4$ can be used. Thus, $NH_3$ as one compound of the formula IIIa also includes $NH_4^+$ ions which will always be present in the reaction solution in dependence of the pH value of the solution. Preferably the diketone of the formula II is reacted with $CH_3COONH_4$. The reaction can be carried out in any common inert solvent such as THF preferably at elevated temperatures, such as, for example, under reflux.

In one embodiment the reaction is conducted with ammonium acetate in refluxing THF for about 6 hours. The yield of this reaction is considerably higher than the yield of the similar reaction with benzylamine instead of ammonium acetate.

Instead of $NH_3$ a primary amine (formula IIIa), an amine derivative with carbon dioxide (formula IIIb) or a silylated amine (formula IIIc) can be employed in the process of the present invention. In this case the substituent $R^1$ is not particularly limited and can be chosen among the hydrocarbon groups defined above for $R^1$. Preferably $R^1$ is a straight or branched, saturated or unsaturated $C_{1-20}$ hydrocarbon group, in particular $C_{1-20}$ alkyl group, which may comprise 1-5 oxygen atoms, may be substituted with 1-5 optionally protected hydroxy groups, 1 or 2 —$NR^8R^9$ residues (wherein $R^8$ and $R^9$ are defined as above) and/or 1 or 2 optionally protected carboxy groups, in which hydrocarbon group 1-5 carbon atoms may form carbonyl groups and which hydrocarbon group or part of which hydrocarbon group may form 1 or more rings.

In one embodiment of the process of the present invention $R^1$ is a residue of the formula X

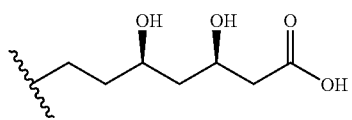

which may optionally be protected or is chosen such that it can easily be converted into a residue of the formula X. Residues which can be converted into residues of the formula X are for example known from WO 2004/046105, WO 94/20492, WO 02/057274, WO 02/055519, EP-A-0 330 172, EP-A-0 179 559, EP-A-0 247 633 and EP-A-0 409 281. The disclosures of these documents are therefore incorporated by reference herein.

Preferred residues for $R^1$ are selected from the following residues:

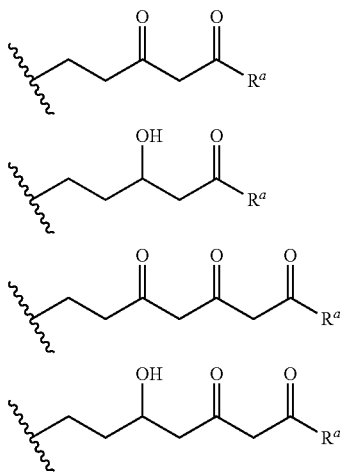

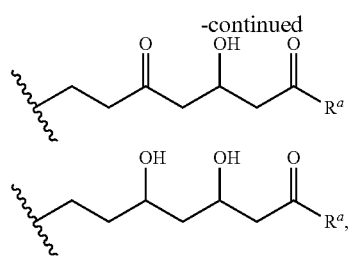

wherein $R^a$ is —$OR^b$, —$SR^c$, $SeR^d$ or —$NR^eR^f$;
$R^b$, $R^c$ and $R^d$ are independently selected from straight, branched and/or cyclic, saturated or unsaturated $C_{1-10}$ alkyl residue, aryl residue or arylalkyl residue;
$R^e$ and $R^f$ are independently selected from straight, branched and/or cyclic, saturated or unsaturated $C_{1-10}$ alkyl residue, aryl residue or arylalkyl residue or
$R^e$ and $R^f$ taken together are

—$(CH_2)_4$—

—$(CH_2)_5$—

—$(CH(R^g)$—$CH_2)_3$—

—$(CH(R^g)$—$CH_2)_4$—

—$(CH(R^g)$—$(CH_2)_2$—$CH(R^g))$—

—$(CH(R^g)$—$(CH_2)_3$—$CH(R^g))$—

—$CH_2$—$CH_2$-A-$CH_2$—$CH_2$—

—$CH(R^g)$—$CH_2$-A-$CH_2$—$CH_2$—

—$CH(R^g)$—$CH_2$-A-$CH_2$—$CH(R^g)$—, wherein $R^g$ is $C_{1-4}$ alkyl residue and A is O, S or $NR^h$, wherein $R^h$ is hydrogen or $C_{1-4}$ alkyl residue;
and each hydroxy group may independently be protected with a suitable protecting group whereby two hydroxy groups together with their protecting group may form a ring. It is understood that any of the residues $R^1$ can be, if possible, in its lactone or lactame form.

As protecting groups for the optionally protected hydroxy groups and the optionally protected carboxy groups usual protecting groups known to the person skilled in the art may be used. Suitable protecting groups are exemplified in WO 03/044011, which therefore is incorporated by reference herein.

In the compound of the formula II $R^2$ may be —$OR^3$, —$NR^4R^5$ or halogen, preferably —$OR^3$ or halogen and most preferred —$OR^3$. Herein $R^3$, $R^4$ and $R^5$ are defined as above.

For $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^b$, $R^c$, $R^d$, $R^e$ and $R^f$ the alkyl residue is preferably a straight or branched, saturated or unsaturated $C_{1-6}$ alkyl residue or a cyclic $C_{3-6}$ alkyl residue, such as methyl, ethyl, n-propyl, iso-propyl, n-butyl, iso-butyl, tert-butyl, pentyl, n-hexyl or cyclohexyl. Preferred aryl residues are phenyl and naphthyl, particularly preferred phenyl. The aryl residue furthermore includes heteroaryl residues such as pyrrole or pyridine. The preferred arylalkyl residue is benzyl.

For R$^{17}$, R$^{18}$ and R$^{19}$ the alkyl residue is preferably a straight or branched C$_{1-6}$ alkyl residue or a cyclic C$_{3-6}$ residue, such as methyl, ethyl, n-propyl, iso-propyl, n-butyl, iso-butyl, tert-butyl, pentyl, n-hexyl or cyclohexyl. Preferred aryl residues are phenyl and naphthyl, particularly preferred phenyl. The aryl residue furthermore includes heteroaryl residues such as pyrrole or pyridine.

In the present application halogen stands for fluoro, chloro, bromo or iodo, preferably chloro or bromo.

The primary amine of the formula IIIa or the amines of the formulae IIIb or IIIc are reacted with a diketone of the formula II. This reaction can for example be carried out under the same conditions as described above for the reaction, wherein the compound of the formula IIIa is NH$_3$. Further detailed reaction conditions can for example be found in WO 2004/046105, WO 94/20492 and EP-A-0 330 172. For example, the reaction can be conducted under heating with azeotropical water removed in an appropriate solvent or mixture of solvents catalyzed with an acid, such as, for example, pivalic acid. As suitable solvents n-heptane, toluene and THF or mixtures thereof can be mentioned. Alternatively the reaction can be conducted without any solvent (neat) under heating the reactants to for example about 120° C. to 140° C.

When reacting a compound of the formula II, wherein R$^2$ is —OR$^3$ or halogen with a compound of the formulae IIIa, IIIb or IIIc a by-product of the following formula IV

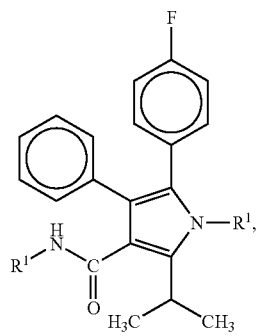

IV wherein R$^1$ at both occurrences are identical and defined as above may be obtained. In this case the desired pyrrole derivative of the formula I may be separated from the reaction by-product of the formula IV, and the reaction by-product can subsequently be converted into a pyrrole derivative of the formula I, wherein R$^2$ is —OR$^3$, —NR$^4$R$^5$ or halogen and R$^3$, R$^4$ and R$^5$ are defined as above, provided that —NR$^4$R$^5$ is different from —NHR$^1$. This reaction route is effective for recycling undesired by-products obtained in the reaction between the diketone of the formula II and the amine of the formula III.

In a further embodiment of the process of the present invention the compound of the formula II is obtained by
a) reacting a compound of the formula V

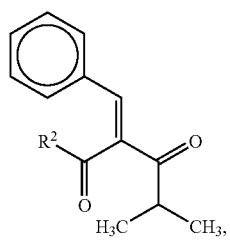

V wherein R$^2$ is defined as in claim 1,
with 4-fluorobenzaldehyde or
b) reacting a compound of the formula VI

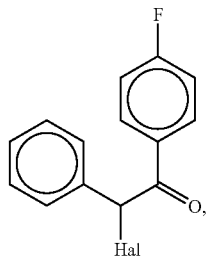

VI wherein Hal is halogen, preferably bromo with a compound of the formula VII

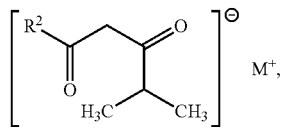

VII wherein R$^2$ is defined as in claim 1 and M$^+$ is selected from H$^+$, Li$^+$, Na$^+$ and K$^+$, preferably Na$^+$.

The above reaction route a) has the advantage that the compound of the formula V, wherein R$^2$ is —OR$^3$ can be easily purified by distillation. Thus, this intermediate can be employed in the following reaction in a highly pure form.

The above reaction route b) has the advantage that the compound of the formula VI can easily be obtained from the commercially available 2-[2-(4-fluorophenyl)-2-oxo-1-phenyl-ethyl]-4-methyl-3-oxo-pentanoic acid phenylamide by cleavage with hydrogen peroxide in the presence of a base such as NaOH.

Above reaction a) can for example be carried out under solvent-free conditions catalyzed by 2-(2-hydroxyethyl)-3-methyl-4-ethylthiazolium bromide in the presence of triethylamine under heating to for example to a temperature of about 60° C. to about 80° C.

In reaction route a) the compound of the formula V can be obtained by reacting a compound of the formula IX

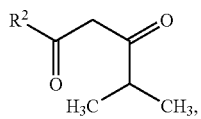

IX wherein R$^2$ is defined as above with benzaldehyde. This reaction can be carried out in the presence of a catalyst such as, for example, piperidine and glacial acetic acid, ethylene diamine and glacial acetic acid, β-alanine and glacial acetic acid, and the like in an inert solvent such as, for example, toluene, heptane, hexane, and the like for about 24 to about 36 hours at about 60° C. to about 120° C. with the removal of water to afford a compound of the formula V.

If in the compound of the formula V R$^2$ is —OR$^3$, this compound is heat-stable and can be distilled as to separate the desired compound of the formula V from undesired by-products of the reaction. In a preferred embodiment of the process of the present invention the reaction between the compound of the formula IX and benzaldehyde is catalyzed with β-alanine in the presence of acetic acid, preferably glacial acetic acid, in toluene. The reaction mixture is heated under reflux with azeotropic removal of water for about 24 hours. After usual workup the product can be distilled under reduced pressure.

In the alternative embodiment according to above route b) the compound of the formula II is obtained by reacting the compounds of the formula VI and VII with each other. This addition reaction can be carried out in any suitable inert organic solvent, preferably anhydrous inert organic solvent, such as, for example, ethers, e.g. diethyl ether, 1,2-diethoxyethane, 1,2-dimethoxyethane, THF or mixtures thereof. Preferably the reaction is carried out in THF. The reaction temperature may be in the range of for example about 0° C. to about 40° C., preferably from about 0° C. to about room temperature.

In a preferred embodiment the compound of the formula VII is prepared in situ.

The compound of the formula VI can be obtained by halogenating the compound of the formula VIII

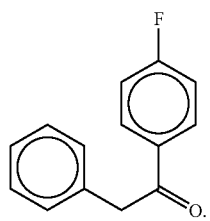

VIII

Halogenation, preferably bromination of the compound of the formula VIII can be carried out with for example bromine in an inert organic solvent, preferably an anhydrous inert organic solvent, such as, for example, halogenated lower alkane solvents, e.g. CCl$_4$, CHCl$_3$, 1,1-dichloroethane, 1,2-dichloroethane, methylene chloride, 1,1,2-trichloroethane or mixtures thereof. A preferred solvent is CHCl$_3$. The reaction can be carried out for example at a temperature of about 0° C. to about 40° C.

The compound of the formula VIII can be obtained by cleavage of a compound of the formula II, wherein R$^2$ is —NR$^4$R$^5$, and R$^4$ and R$^5$ are defined as above, such as the commercially available 2-[2-(4-fluorophenyl)-2-oxo-1-phenyl-ethyl]-4-methyl-3-oxo-pentanoic acid phenylamide. The cleavage can be carried out for example with hydrogen peroxide in the presence of a base such as NaOH.

A particularly advantageous route for the synthesis of a compound of the formula II is shown in the following scheme:

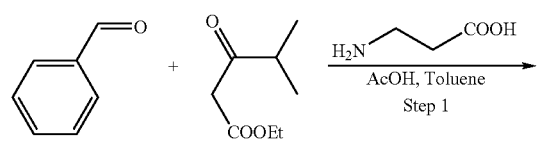

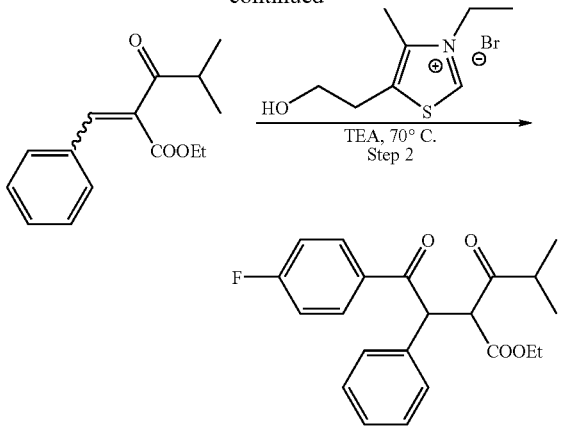

Advantages of the synthesis of diketone ethyl ester by this route are:
- no need of reaction solvent in step 2 (environmental, economic);
- no need of recrystallization process in step 1 (environmental, economic), product is isolated by distillation;
- this is the shortest synthetic route (only 2 steps) in comparison with other known processes (3-5 steps required);
- in the process for the step 1 nontoxic catalyst (β-alanine) is used (environmental);
- no need of toxic a corrosive reagents (like bromine in alternative route);
- all starting materials are commercially available.

The present invention further relates to compounds of the formula I, II and IV, wherein R$^2$ is —OR$^3$ or halogen and R$^1$ at both occurrences are identical and defined as above, respectively. These compounds are useful intermediates in the preparation of atorvastatin.

The present invention will now be further illustrated by the following examples which are not intended to be limiting.

EXAMPLES

1. Synthesis of ethyl-2-benzylidene-4-methyl-3-oxopentanoate (compound of formula V)

A mixture of benzaldehyde (33.8 g, 319 mmol), ethyl isobutyrylacetate (50.4 g, 319 mmol), β-alanine (1.0 g) and acetic acid (10 ml) in 600 ml of toluene was stirred and heated under reflux with azeotropic removal of water (Dean-Stark adapter) until GC analysis showed no presence of starting material (24 h). The solution was cooled, poured into ethylacetate (400 ml), washed with 1 M HCl solution (2×100 ml), saturated NaHCO$_3$ solution (2×100 ml) and brine (100 ml) and dried over anhydrous Na$_2$SO$_4$. The solvent was removed under reduced pressure to yield 76.3 g of brown oil which was further distilled under reduced pressure (bp 105-120° C./0.06 mm Hg) to afford 58.9 g (75%) of ethyl 2-benzylidene-4-methyl-3-oxopentanoate as a mixture of isomers (major ~70%).

2. Synthesis of ethyl 2-[2-(4-fluorophenyl)-2-oxo-1-phenyl-ethyl]-4-methyl-3-oxopentanoate (compound of formula II)

To a stirred mixture of ethyl 2-benzylidene-4-methyl-3-oxopentanoate (52.5 g, 0.213 mol), 4-fluorobenzaldehyde (39.7 g, 0.320 mol) and 2-(2-hydroxyethyl)-3-methyl-4-ethylthiazolium bromide (8.11 g, 0.032 mol) was added dropwise triethylamine (21.3 ml). The solution turned dark and precipitation of solid particles was observed. A mixture was then heated at 70° C. until the reaction mixture did not contain starting ethyl 2-benzylidene-4-methyl-3-oxopentanoate (HPLC monitoring). After cooling to room temperature, the mixture was diluted with ethylacetate (500 ml) and water (100 ml). The organic phase was washed with 1 M HCl solution (2×100 ml), saturated NaHCO$_3$ solution (2×100 ml) and brine (100 ml) and dried over anhydrous Na$_2$SO$_4$. The solvent was removed under reduced pressure to yield 100.2 g of impure oily product which was then dissolved in dichloromethane (400 ml) and silicagel (50 g) was added. The mixture was stirred for 10 minutes and the silicagel was filtered off and washed with dichloromethane (500 ml). Air was bubbled through the combined filtrates for 24 hours in order to oxidize remaining 4-fluorobenzaldehyde. Additional 200 ml of dichloromethane was added to the reaction mixture to compensate losses due to evaporation and the solution was washed with saturated NaHCO$_3$ solution (2×100 ml) and water (100 ml) and dried over anhydrous Na$_2$SO$_4$. The solvent was removed under reduced pressure to yield 87 g yellow oily product which slowly solidified. The oily product contains 85% of ethyl 2-[2-(4-fluorophenyl)-2-oxo-1-phenyl-ethyl]-4-methyl-3-oxopentanoate and the calculated yield was then 94%.

3. Synthesis of ethyl 5-(4-fluorophenyl)-2-isopropyl-1-phenethyl-4-phenyl-1H-pyrrole-3-carboxylate (compound of the formula I)

Ethyl 2-[2-(4-fluorophenyl)-2-oxo-1-phenyl-ethyl]-4-methyl-3-oxopentanoate (reagent 1) was reacted with 2-phenyl-ethylamine (reagent 2) under the conditions summarized in the following table 1.

TABLE 1

| Exp. No.: | Ratio of reagents 1:2:catalyst | Catalyst | Solvents | Conditions | Reaction time [h] | Yield [%] |
|---|---|---|---|---|---|---|
| 1 | 1:1:1 | Pivalic acid | n-heptane, THF, toluene | Reflux with azeotropic water removal | 96 | 72.4 |
| 2 | 1:1:2 | Pivalic acid | — | Heating neat at 125-130° C. | 48 | 65.0 |
| 3 | 1:1.5:1.5 | Pivalic acid | n-heptane, THF, toluene | Reflux with azeotropic water removal | 24 | 68.5 |

The invention claimed is:
1. A process for preparing a pyrrole derivative of the formula I

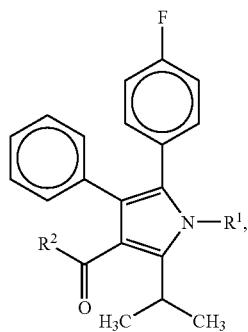

wherein

R$^1$ is hydrogen or a straight or branched, saturated or unsaturated C$_{1-30}$ hydrocarbon group which may comprise 1-5 oxygen atoms, 1-5 nitrogen atoms, 1-2 sulfur atoms, 1 selenium atom and/or 1-5 —NR$^6$ groups, which hydrocarbon group may be substituted with 1-5 optionally protected hydroxy groups, 1-5 —OR$^7$ groups, 1-5 —NR$^8$R$^9$ groups, 1-5 halogen atoms and/or 1-5 optionally protected carboxy groups, in which hydrocarbon group 1-5 carbon atoms may form carbonyl groups and which hydrocarbon group or part of which hydrocarbon group may form one or more rings, R$^2$ is —OR$^3$, —NR$^{10}$CONR$^{11}$R$^{12}$, —NR$^{13}$OR$^{14}$, —ONR$^{15}$R$^{16}$ or halogen, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$ and R$^{16}$ are independently selected from hydrogen or a straight, branched and/or cyclic, saturated or unsaturated C$_{1-10}$ alkyl groups or aryl groups, both groups being optionally substituted with 1-3 optionally protected hydroxy or carboxy groups, 1-3 —OR$^7$ groups, 1-3 —NR$^8$R$^9$ groups and/or 1-3 halogen atoms, the C$_{1-10}$ alkyl group optionally comprising 1-3 oxygen atoms, 1-3 nitrogen atoms and/or 1-3 —NR$^6$ groups, the C$_{1-10}$ alkyl group further optionally comprising or being substituted with 1 or 2 aryl groups, or a salt thereof, which process comprises the steps of reacting a compound of the formula II

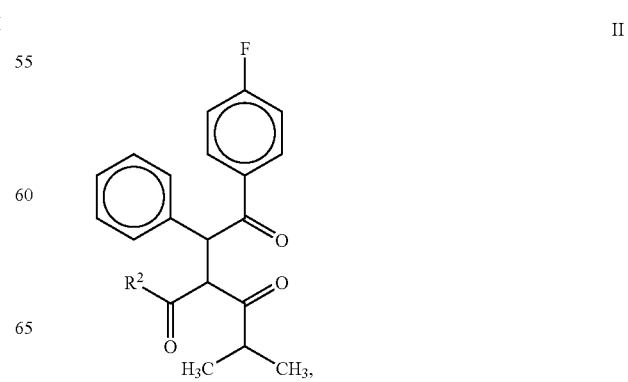

wherein
R² is defined as above, or a salt thereof, with a compound of the formulae IIIa, IIIb or IIIc

   IIIa,

   IIIb

   IIIc, or mixtures thereof, wherein R¹ is defined as above,

R¹⁷ and R¹⁸ are independently selected from straight, branched and/or cyclic $C_{1-10}$ alkyl group or aryl group; and R¹⁹ is straight, branched and/or cyclic $C_{1-10}$ alkyl group, aryl group or —NH—R¹, and, if necessary, converting the obtained pyrrole derivative having the substituent R¹ into a pyrrole derivative having a different substituent R¹.

2. The process according to claim 1, wherein R² is —OR³ or halogen.

3. The process according to claim 2, which comprises the additional step of separating the pyrrole derivative of the formula I from the reaction by-product of the formula IV

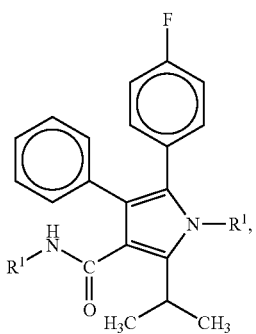   IV wherein R¹ at both occurrences are identical.

4. The process according to claim 3, which comprises the additional step of converting the separated reaction by-product of the formula IV into a pyrrole derivative of the formula I, wherein R² is —OR³ or halogen.

5. The process according to claim 1, wherein the compound of formula II is obtained by
a) reacting a compound of the formula V

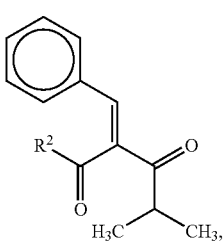   V wherein R² is defined as in claim 1, with 4-fluorobenzaldehyde or
b) reacting a compound of the formula VI

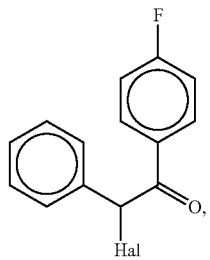   VI wherein Hal is halogen, with a compound of the formula VII

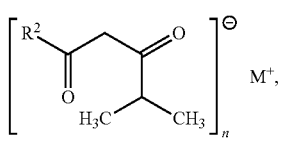   VII wherein R² is defined as in claim 1 and M⁺ is selected from H⁺, Li⁺, Na⁺ and K⁺.

6. The process according to claim 5, wherein the compound of the formula VI is obtained by halogenating the compound of the formula VIII

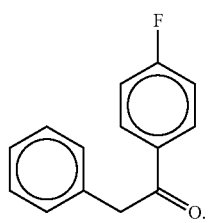   VIII

7. The process according to claim 6, wherein the compound of the formula VIII is obtained by cleavage of a compound of the formula II.

8. The process according to claim 5, wherein the compound of the formula V is obtained by reacting a compound of the formula IX

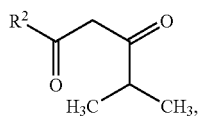   IX with benzaldehyde.

9. The process according to claim 1, wherein R¹ is a straight or branched, saturated or unsaturated $C_{1-20}$ hydrocarbon group which may comprise 1-5 oxygen atoms, may be substituted with 1-5 optionally protected hydroxy groups, 1 or 2 —NR⁸R⁹ groups (wherein R⁸ and R⁹ are defined as in claim 1) and/or 1 or 2 optionally protected carboxy groups, in which hydrocarbon group 1-5 carbon atoms may form carbonyl groups and which hydrocarbon group or part of which hydrocarbon group may form one or more rings.

10. The process according to claim 1, wherein $R^3$, $R^4$, $R^5$, $R^6$, $R^7$, $R^8$ and $R^9$ are independently selected from hydrogen, a straight or branched, saturated or unsaturated $C_{1-6}$ alkyl group, a cyclic $C_{3-6}$ alkyl group or phenyl.

* * * * *

UNITED STATES PATENT AND TRADEMARK OFFICE
CERTIFICATE OF CORRECTION

| | | |
|---|---|---|
| PATENT NO. | : 7,932,403 B2 | |
| APPLICATION NO. | : 11/722318 | |
| DATED | : April 26, 2011 | |
| INVENTOR(S) | : Pavel Bobal et al. | |

It is certified that error appears in the above-identified patent and that said Letters Patent is hereby corrected as shown below:

At column 3, line 35, please correct the recitation of the R2 group listed as "$NR^{10}NR^{11}R^{12}$" to corrected read -- $NR^{10}CONR^{11}R^{12}$ --.

At column 4, line 63, please correct the ammonium salt listed as "$NH_4C_1$" to correctly read -- $NH_4Cl$ --.

Signed and Sealed this
Twenty-third Day of August, 2011

David J. Kappos
*Director of the United States Patent and Trademark Office*